(12) United States Patent
Mrowka et al.

(10) Patent No.: US 9,783,786 B2
(45) Date of Patent: Oct. 10, 2017

(54) METHOD FOR ACTIVATING OCT4 FOR INDUCTION OF PLURIPOTENT STEM CELLS

(75) Inventors: Ralf Mrowka, Jena (DE); Gunter Wolf, Jena (DE); Stefan Wölfl, Dossenheim (DE); Xinlai Cheng, Kaiserslautern (DE)

(73) Assignees: UNIVERSITATSKLINIKUM JENA, Jena (DE); Stefan Wölfl, Dossenheim (DE)

( * ) Notice: Subject to any disclaimer, the term of this patent is extended or adjusted under 35 U.S.C. 154(b) by 230 days.

(21) Appl. No.: 14/411,506

(22) PCT Filed: Jun. 29, 2012

(86) PCT No.: PCT/EP2012/062725
§ 371 (c)(1),
(2), (4) Date: May 31, 2015

(87) PCT Pub. No.: WO2014/000814
PCT Pub. Date: Jan. 3, 2014

(65) Prior Publication Data
US 2015/0267173 A1    Sep. 24, 2015

(51) Int. Cl.
*C12N 5/02*     (2006.01)
*C12N 5/074*    (2010.01)

(52) U.S. Cl.
CPC ...... *C12N 5/0696* (2013.01); *C12N 2501/603* (2013.01); *C12N 2501/605* (2013.01); *C12N 2501/999* (2013.01); *C12N 2506/09* (2013.01); *C12N 2506/11* (2013.01); *C12N 2506/1315* (2013.01); *C12N 2506/1323* (2013.01); *C12N 2506/14* (2013.01); *C12N 2506/25* (2013.01)

(58) Field of Classification Search
None
See application file for complete search history.

(56) References Cited

FOREIGN PATENT DOCUMENTS

| WO | WO 2011/019957 | 2/2011 |
|----|----------------|--------|
| WO | WO 2011/159692 | 12/2011 |

OTHER PUBLICATIONS

Zhu et al. Cell Stem Cell. (2010) 7(6): 1-9: 651-655.*
Supplemental Information for Zhu et al. Cell Stem Cell (2010) 7(6): 1-9: 651-655; pp. 1-10.*
Xu Yuan et al: "Brief Report: Combined Chemical Treatment Enables Oct4-Induced Reprogramming from Mouse Embryonic Fibroblasts", Stem Cells, v61.29, No. 3, Mar. 1, 2011.
Yanqin Li et al: "Generation of iPSCs from mouse fibroblasts with a single gene, Oct4, and small molecules", Cell Research, vol. 21, No. 1, Oct. 19, 2010, pp. 196-204.

* cited by examiner

*Primary Examiner* — Susan Hanley
(74) *Attorney, Agent, or Firm* — JMB Davis Ben-David

(57) ABSTRACT

The invention relates to a method for inducing pluripotent stem cells, wherein a mammalian cell is contacted with a compound characterized by a general formula 1 wherein $R^1$ is $(CH_2)_m E$, with E being CCH or CN and m being 0, 1, or 2, and $R^2$ is selected from F, Cl, Br, $OR^3$ and $R^3$, with $R^3$ being selected from H, $(CH_yF_{2-y})_n CH_xF_{3-x}$, with n=0 or 1. The invention further relates to stem cells obtained by the method of the invention, and culture media comprising the compound of the invention.

19 Claims, 5 Drawing Sheets

A

B

A

B

A

B)

SEQUENCE LISTING

<160> NUMBER OF SEQ ID NOS: 12

<210> SEQ ID NO 1
<211> LENGTH: 20
<212> TYPE: DNA

<213> ORGANISM: Homo sapiens

<400> SEQUENCE: 1
gaagttggag aaggtggaac                                           20

<210> SEQ ID NO 2
<211> LENGTH: 21
<212> TYPE: DNA
<213> ORGANISM: Homo sapiens

<400> SEQUENCE: 2
ggtgatcctc ttctgcttca g                                         21

<210> SEQ ID NO 3
<211> LENGTH: 20
<212> TYPE: DNA
<213> ORGANISM: Homo sapiens

<400> SEQUENCE: 3
gaactgtgtt ctcttccacc                                           20

<210> SEQ ID NO 4
<211> LENGTH: 22
<212> TYPE: DNA
<213> ORGANISM: Homo sapiens

<400> SEQUENCE: 4
cacctgtttg tagctgaggt tc                                        22

<210> SEQ ID NO 5
<211> LENGTH: 20
<212> TYPE: DNA
<213> ORGANISM: Homo sapiens

<400> SEQUENCE: 5
caagacgctc atgaagaagg                                           20

<210> SEQ ID NO 6
<211> LENGTH: 22
<212> TYPE: DNA
<213> ORGANISM: Homo sapiens

<400> SEQUENCE: 6
catgtgcgcg taactgtcca tg                                        22

<210> SEQ ID NO 7
<211> LENGTH: 21
<212> TYPE: DNA
<213> ORGANISM: Homo sapiens

<400> SEQUENCE: 7
gatcttcaac gagtccacca g                                         21

<210> SEQ ID NO 8
<211> LENGTH: 24
<212> TYPE: DNA
<213> ORGANISM: Homo sapiens

```
<400> SEQUENCE: 8
gaaaggtggg agatcctcct cttc                                          24

<210> SEQ ID NO 9
<211> LENGTH: 21
<212> TYPE: DNA
<213> ORGANISM: Homo sapiens

<400> SEQUENCE: 9
gtggatgtct ttgtgcacca g                                             21

<210> SEQ ID NO 10
<211> LENGTH: 20
<212> TYPE: DNA
<213> ORGANISM: Homo sapiens

<400> SEQUENCE: 10
gacacggatg gattccagac                                               20

<210> SEQ ID NO 11
<211> LENGTH: 23
<212> TYPE: DNA
<213> ORGANISM: Homo sapiens

<400> SEQUENCE: 11
ctgactacct catgaagatc ctc                                           23

<210> SEQ ID NO 12
<211> LENGTH: 22
<212> TYPE: DNA
<213> ORGANISM: Homo sapiens

<400> SEQUENCE: 12
cattgccaat ggtgatgacc tg                                            22
```

METHOD FOR ACTIVATING OCT4 FOR INDUCTION OF PLURIPOTENT STEM CELLS

CROSS-REFERENCE TO RELATED APPLICATION

This is the U.S. National Stage of International Application No. PCT/EP2012/062725, filed Jun. 29, 2012, and which was published in English under PCT Article 21(2).

The present invention relates to a method for inducing mammalian cells in cell culture to become pluripotent stem cells.

Stem cells, in particular embryonic stem cells, which can be expanded indefinitely and are pluripotent, have attracted considerable attention as a therapeutic approach for treating for example diabetes, cardiovascular-, neurological-, and liver-based diseases. However, the use of inner cell mass-derived embryonic stem cells in cell replacement therapy remains problematic for a number of reasons, including host rejection of allogeneic cells. Moreover, human ESCs are also associated with ethical issues regarding the use of human embryos.

As a means of overcoming the problem of host rejection, autologous induced pluripotent stem (iPS) cells were proposed. As a "proof of principle", cells derived from mouse tail-tip fibroblasts were successfully induced to pluripotency employing retroviral-mediated transduction of Oct4, Sox2, Klf4 and c-Myc. These studies clearly demonstrated that viral transduction of stemness factors is a powerful approach for deriving patient-specific iPS cells to provide tissue-matched differentiated donor cells for therapy, and a source of cells for research into the pathogenesis of complex disease. It has now been shown that the combined expression of four factors, OCT4 (synonym: POU5F1), SOX2, NANOG and L1N28 is sufficient to reprogram neonatal foreskin and adult human dermal fibroblast into iPS cells. These cells have normal karyotypes, express telomerase activity, express cell surface makers and genes that characterize human ES cells, and maintain the developmental potential to differentiate into advanced derivates of all three primary germ layers.

Induced pluripotent stem cell lines (iPS) promise to provide access to a great variety of clinically relevant subjects, and thus are of great interest in current biomedical research. Pluripotency can be induced in somatic mouse cells by the activation of four genes. Human somatic fibroblasts have been converted to pluripotent cell lined by the activation of the genes Sox2, Nanog, Oct4 and Lin28. (Yu et al., Science; 318: 1917-20.2007).

Since induction of pluripotency relies on activating the cited genes, a challenge in this field is to find methods suitable for gene activation that are suitable to clinical applications. Currently employed methods predominantly rely on viral transfection of constitutively or conditionally expressed. The insertion of viral genetic material into the genome of a cell that is ultimately to be transferred into the patient's body raises safety concerns because of possible interference with biological functions of the cell at the site of insertion, which may at worst result in uncontrolled growth. First, the viral insertion of material is not directed to a specific locus in the genome. An alternative method to induce pluripotency is therefore desirable.

Since many signal transduction processes within the cell rely on interaction of biomolecules that may be mimicked or disrupted by small molecules, in theory even complex biological processes such as the induction of pluripotency might be effected by one or several small "pharmaceutical drug-like" molecules. The advance of ultra-high throughput assaying methods, automated synthesis and in-silico methods to predict possible fit between hypothetical targets and small molecule structures provides the ability to screen large compound libraries for candidate compounds.

In light of the above stated art, the objective of the present invention is to provide methods for the induction of pluripotency in mammalian cells by induction of at least one of the pluripotency genes identified above.

This problem is solved by the subject matter of the independent claims.

By combining library screening of a cellular model with in-silico prediction of chemical space and subsequent validation and optimization of hits, a series of compounds were identified that were able to induce OCT4 and NANOG in mammalian cells, thus enabling the induction of pluripotency in autologous mammalian cells by chemical rather than transgenic means.

According to a first aspect of the invention, a method for inducing a pluripotent mammalian stem cell is provided, comprising the steps of contacting a mammalian donor cell with a compound characterized by a general formula 1

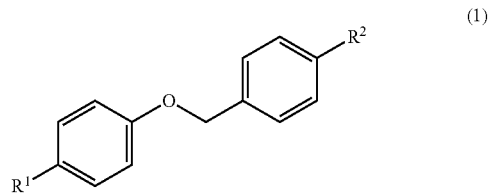

wherein $R^1$ is $(CH_2)_m E$, with E being CCH or CN and m being 0, 1, or 2, and $R^2$ is selected from F, Cl, Br, $NO_2$, $OR^3$ and $R^3$, with $R^3$ being selected from H, $(CH_yF_{2-y})_n CH_xF_{3-x}$ (n being 0 or 1) wherein x equals 0, 1, 2, or 3.

In some embodiments, $R^1$ is CN. In some embodiments, $R^2$ is $OCF_3$, $OCH_3$ or F.

In some embodiments, $R^1$ is $CH_2CN$. In some embodiments, $R^1$ is $CH_2CCH$.

In some embodiments, $R^1$ is $CH_2CN$ and $R^2$ is $OR^3$, with $R^3$ being $(CH_yF_{2-y})_n CH_xF_{3-x}$(n=0 or 1). In some embodiments, $R^1$ is $CH_2CCH$ and $R^2$ is $OR^3$, with $R^3$ being $(CH_yF_{2-y})_n CH_xF_{3-x}$(n=0 or 1).

In one embodiment, the compound employed in the method of the invention is

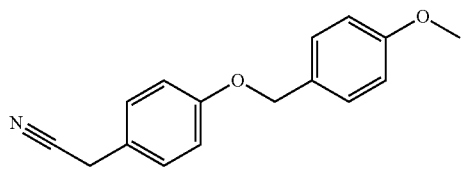

2-[4-[(4-methoxyphenyl)methoxy]phenyl]acetonitrile (2),

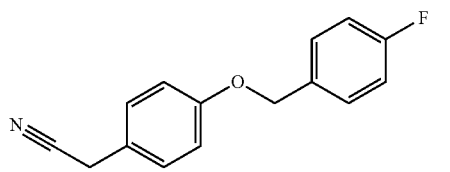

2-[4-[(4-fluorophenyl)methoxy]phenyl]acetonitrile (3),

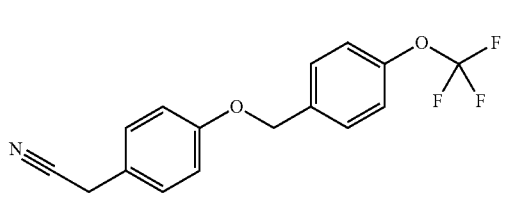

2-[4-[[4-(trifluoromethoxy)phenyl]methoxy]phenyl]acetonitrile (4),

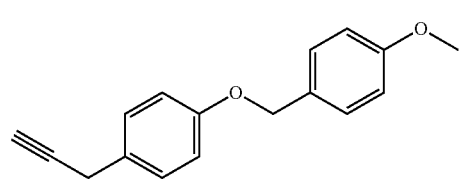

1-methoxy-4-[(4-prop-2-ynylphenoxy)methyl]benzene (5)

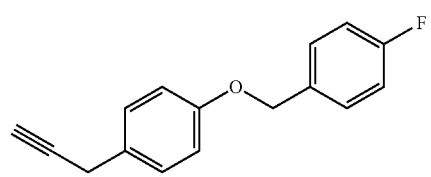

1-fluoro-4-[(4-prop-2-ynylphenoxy)methyl]benzene (6) or

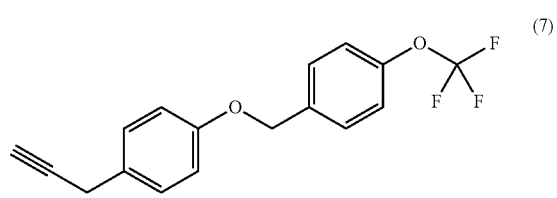 [SMILES: C#CCc1ccc(OCc2ccc(OC(F)(F)F)cc2)cc1]

1-prop-2-ynyl-4[[4-(trifluoromethoxy)phenyl]methoxy]benzene (7).

In one embodiment, the compound is 2-[4-[(4-nitrophenyl)methoxy]phenyl]acetonitrile.

In one embodiment, the compound is 1-nitro-4-[(4-prop-2-ynylphenoxy)methyl]benzene.

The donor cell is not an embryonic cell.

In some embodiments, the donor cell is a cell derived from human tissue skin, intestine, bone, blood, muscle, and other tissue accessible for biopsy or punctuation, or a cell derived from body fluids such as urine, saliva or faeces. The cell may be characterized as fibroblasts but also may be characterized as any other tissue specific cell type.

In some embodiments, the method of the invention comprises the steps of
a. providing the mammalian donor cell ex-vivo in a cell culture medium;
b. adding the compound to achieve a defined final concentration of said compound;
c. maintaining the donor cells under conditions of cell culture for a defined amount of time;
d. collecting the pluripotent mammalian stem cell.

In some embodiments, the defined final concentration is between 1 µmol/l and 25 µmol/l, particularly 1 µmol/l, 2 µmol/l, 3 µmol/l, 4 µmol/l, 5 µmol/l, 6 µmol/l, 7 µmol/l, 8 µmol/l, 9 µmol/l, 10 µmol/l, 11 µmol/l, 12 µmol/l, 13 µmol/l, 14 µmol/l, 15 µmol/l, 20 µmol/l or 25 µmol/l. In some embodiments, the defined final concentration is between 1 µmol/l and 15 µmol/l. In some embodiments, the defined final concentration is between 3 µmol/l and 12 µmol/l.

In some embodiments, the defined amount of time is between 24 hrs and 72 hrs. In some embodiments, the defined amount of time is 5 days, 10 days, 15 days, 20 days, 25 days, 30 days or 40 days. Cells are generally kept in culture until iPS cell formation is achieved. The cells can subsequently be used for differentiation into another phenotype.

In some embodiments, collecting said pluripotent mammalian stem cells comprises a selection step, whereby said pluripotent mammalian stem cells are selected by virtue of their expressing marker genes such as Nanog, Sox2, Lin28, SSEA-4, TRA-1-60, TRA-1-81 or activated enzyme such as Alkaline Phosphatase in combination with negative selection markers such as CD13 in the case of fibroblasts. In some embodiments, CD133 expression is used as a marker to select induced pluripotent stem cells, i.e. cells that express CD133 are selected.

Cells may be selected by any suitable means or method known to the skilled person, such as—by way of non-limiting example—magnetic cell separation (MACS) or fluorescence activated cell sorting (FACS sort).

According to a second aspect of the invention, a pluripotent stem cell is provided that is obtainable or obtained by a method according to the invention.

According to a third aspect of the invention, a cell culture medium comprising a compound characterized by a general formula 1 is provided

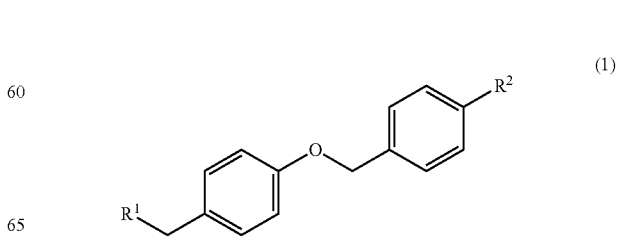

wherein $R^1$ is CCH or CN, and $R^2$ is selected from F, Cl, Br, $OR^3$ and $R^3$, with $R^3$ being selected from H, $(CH_yF_{2-y})_n$ $CH_xF_{3-x}$, wherein n is 0 or 1 wherein x equals 0, 1, 2, or 3, In some embodiments, $R^1$ is CN. In some embodiments, $R^2$ is $OCF_3$, $OCH_3$ or F. In some embodiments, the compound is 2-[4-[(4-methoxyphenyl)methoxy]phenyl]acetonitrile (2);

2-[4-[(4-fluorophenyl)methoxy]phenyl]acetonitrile (3) or

2-[4-[[4-(trifluoromethoxy)phenyl]methoxy]phenyl]acetonitrile (4).

In some embodiments, the compound has a concentration between 1 μmol/l and 25 μmol/l, particularly 1 μmol/l, 2 μmol/l, 3 μmol/l, 4 μmol/l, 5 μmol/l, 6 μmol/l, 7 μmol/l, 8 μmol/l, 9 μmol/l, 10 μmol/l, 11 μmol/l, 12 μmol/l, 13 μmol/l, 14 μmol/l, 15 μmol/l, 20 μmol/l or 25 μmol/l. In some embodiments, the defined final concentration is between 1 μmol/l and 15 μmol/l. In some embodiments, the defined final concentration is between 3 μmol/l and 12 μmol/l.

The invention is further illustrated by the following examples and figures, from which further embodiments and advantages can be drawn.

SHORT DESCRIPTION OF THE FIGURES

Figure 1:
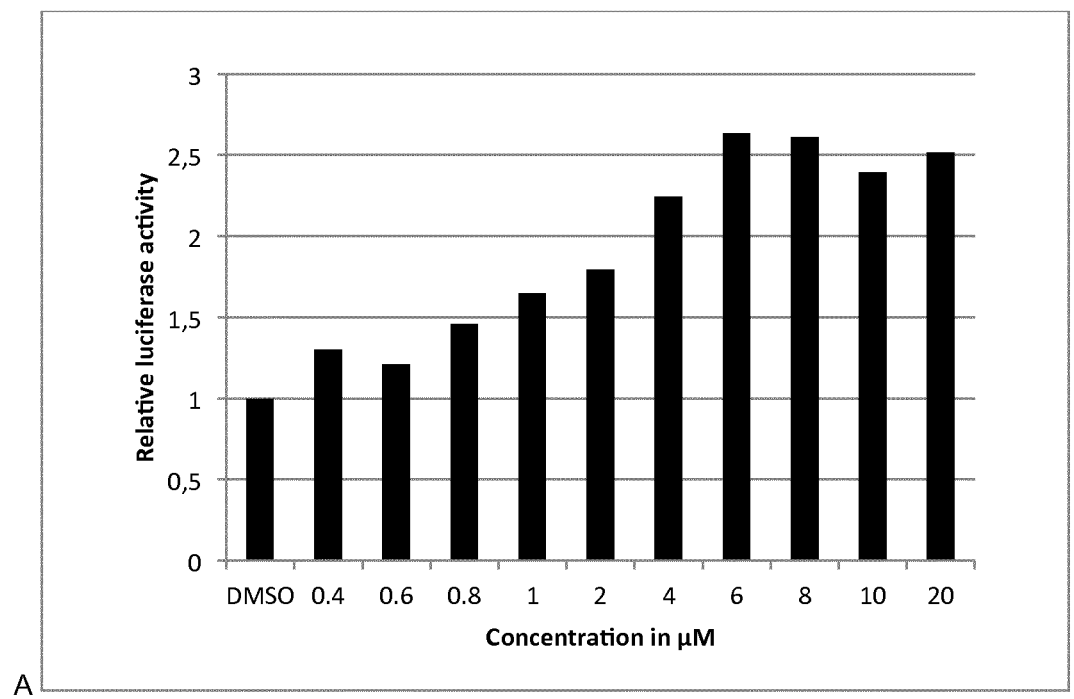
FIG. 1 shows the results of an assay measuring OCT4-promoter driven luciferase expression in HEK293 cells at 48 h (A) and 72 h (B) after stimulation with compound 2.
Figure 1:
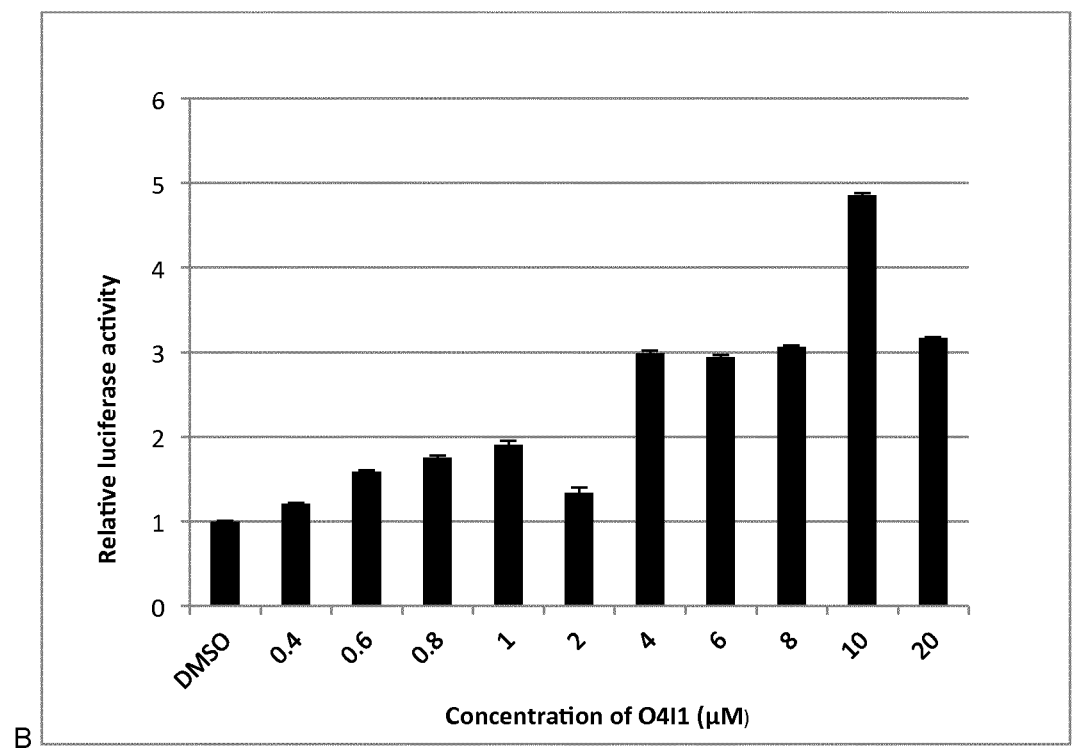
Figure 2:
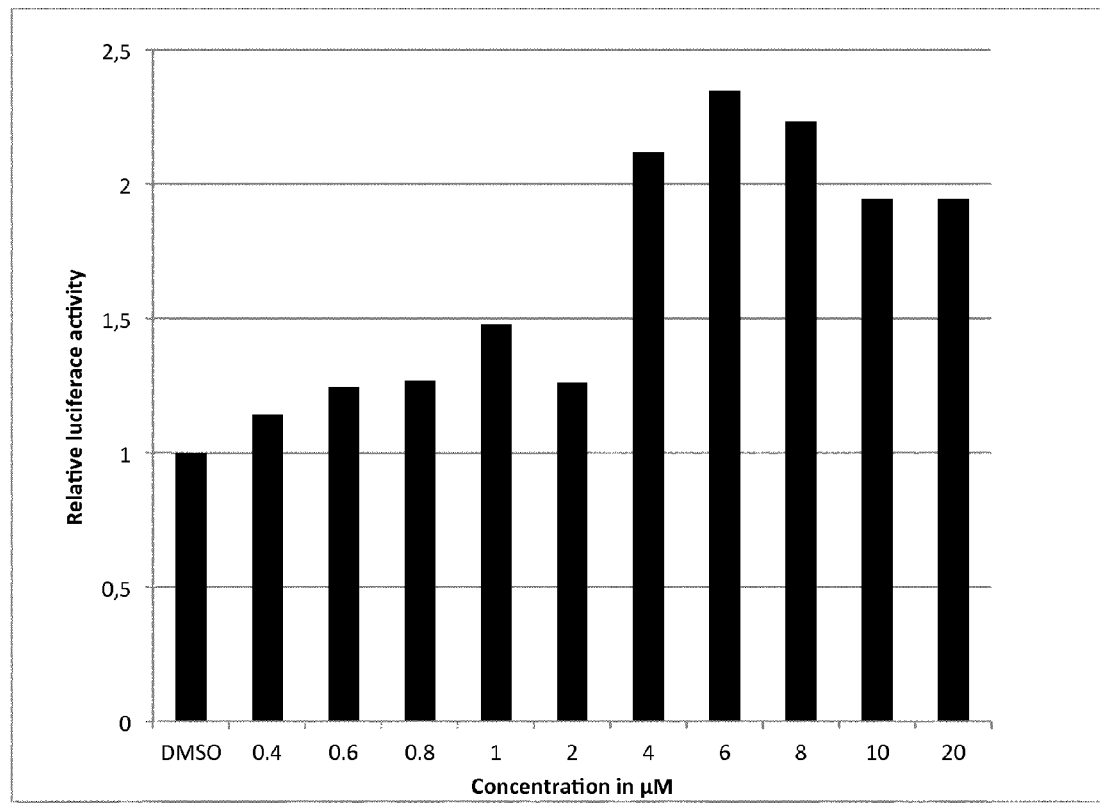
FIG. 2 shows the results of an assay measuring NANOG-promoter driven luciferase expression in HEK293 cells at 48 h after stimulation with compound 2.
Figure 3:
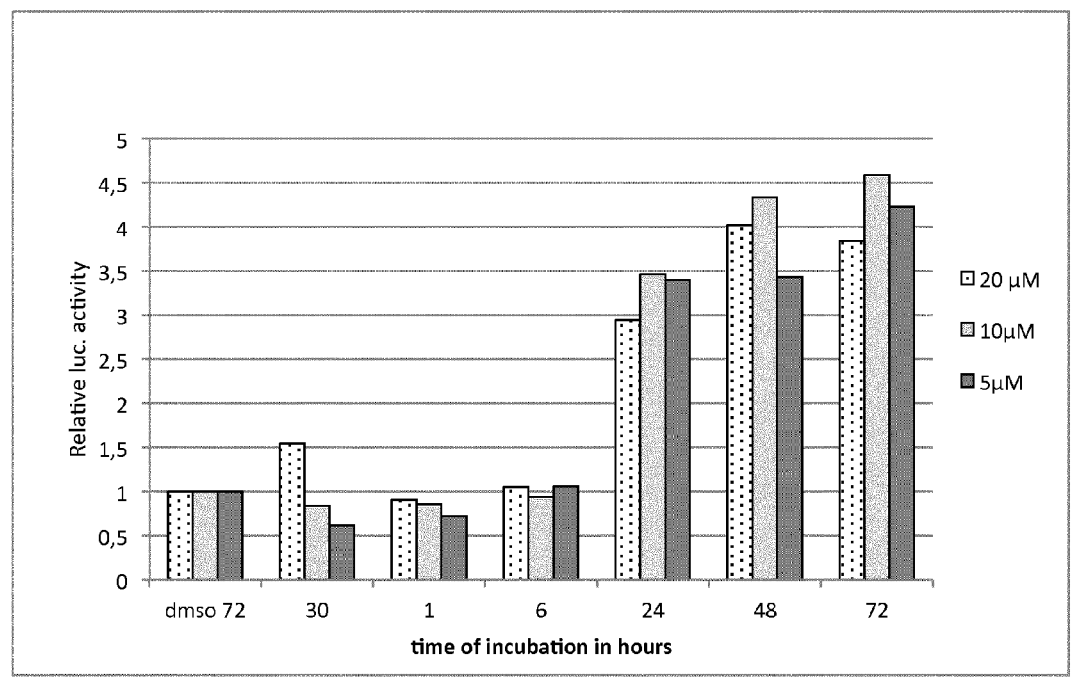
Figure 3:
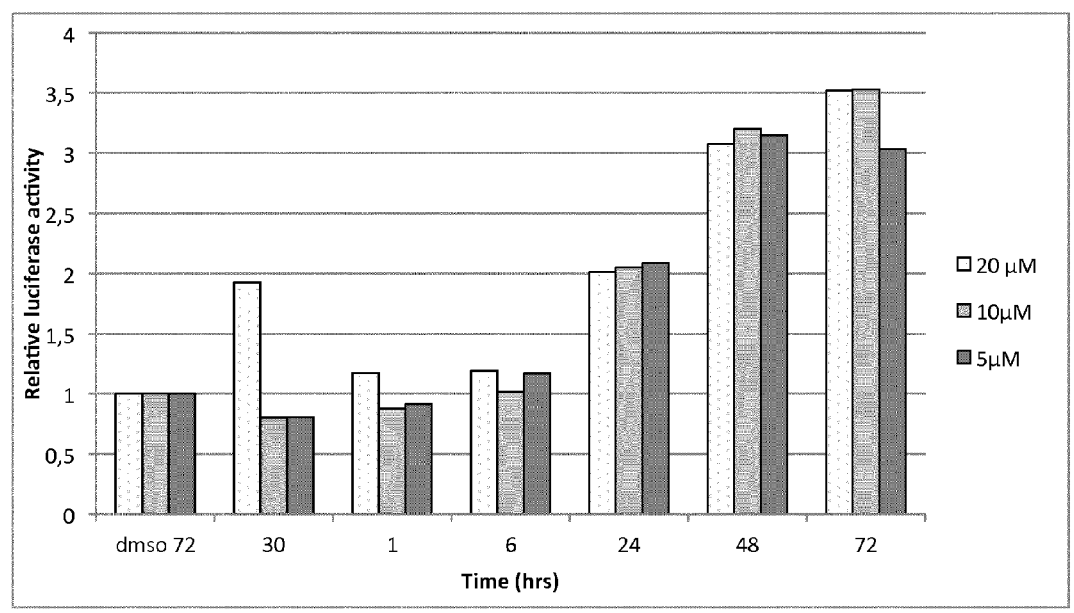

FIG. 3 shows a time course of NANOG-promoter (A) and OCT4-promoter (B) driven luciferase expression after stimulation with compound 2; the number 30 in the x-axis refers to 30 min, the numbers 1, 6, 24, 48 and 72 in the x-axis refer to 1, 6, 24, 48 and 72 hours, respectively.

Figure 4:
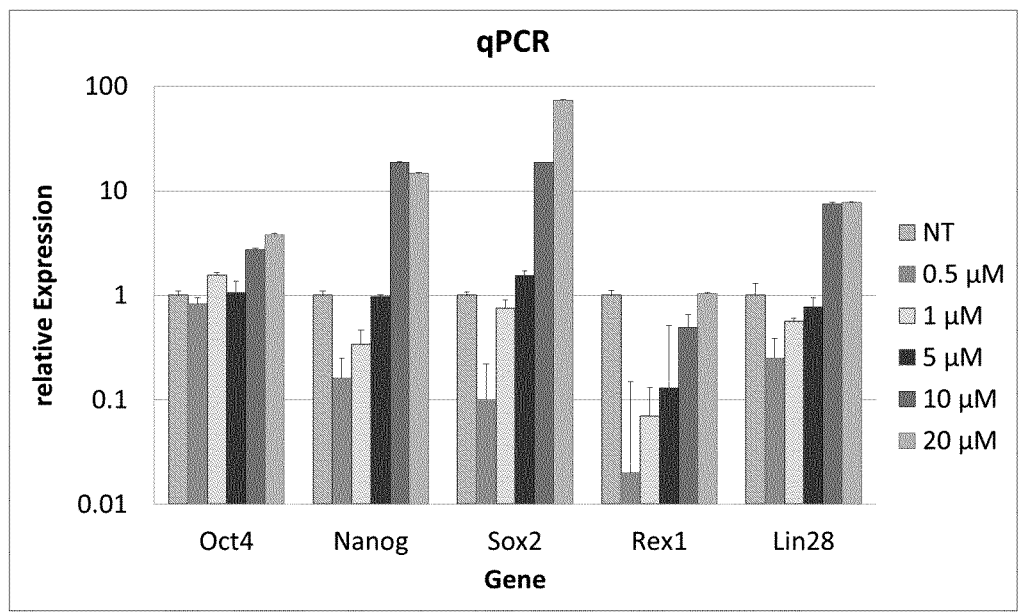

FIG. 4 shows the results of quantitative PCR measurement of stemness factor mRNAs as a function of compound concentration (compound 2) in HEK293 cells. Series of bars refer to (left to right) control, 0.5 μmol/l, 1 μmol/l, 5 μmol/l, 10 μmol/l, 20 μmol/l.

Figure 5:
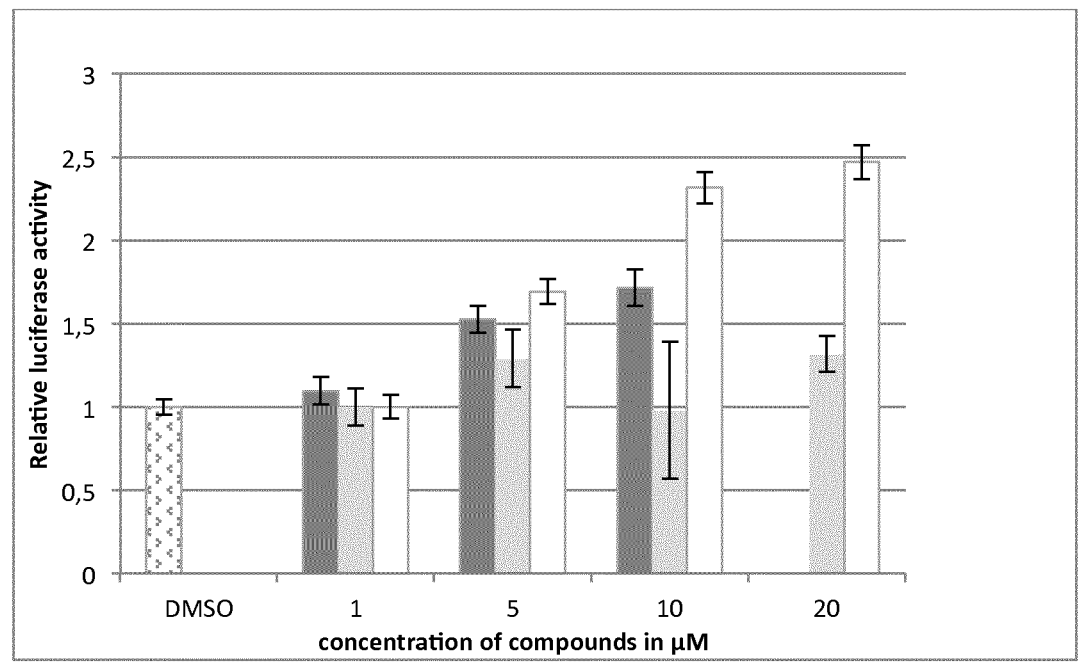
Figure 5:
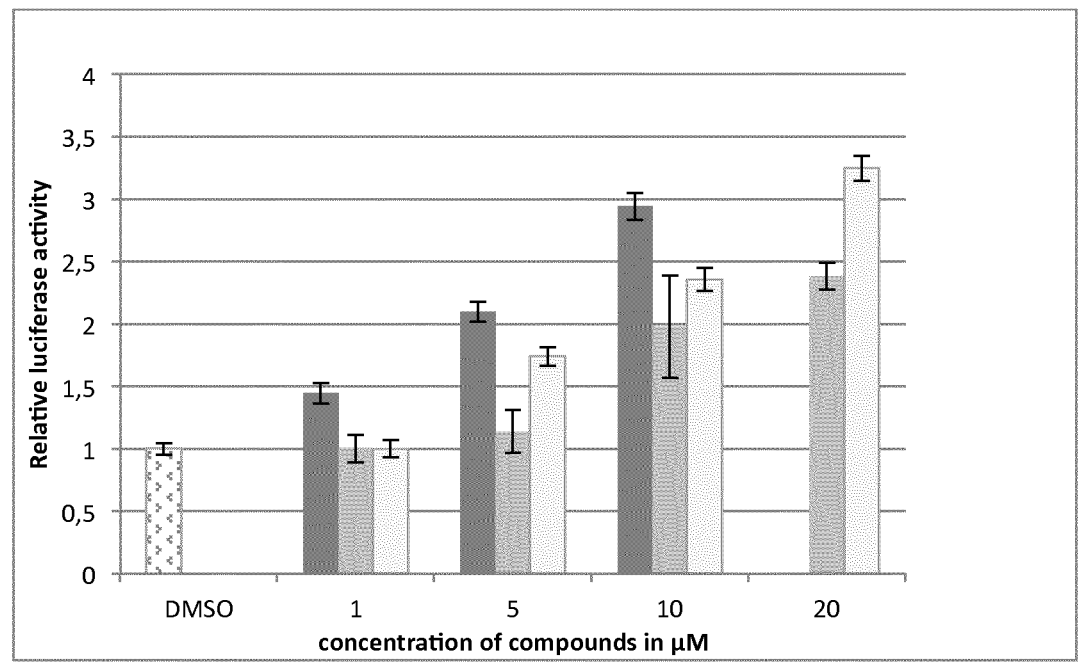

FIG. 5 shows the results of an assay measuring OCT4-promoter (A) and NANOG-promoter (B) driven luciferase expression in HEK293 cells for compound 2,3,4. Series of bars refer to (left to right) control and compound 2 (dark), compound 3 (grey), and compound 4 (bright).

EXAMPLES

Construction of Cell Lines

The promoters of the human Oct4 (Entrez identifier No. 5460) and Nanog (Entrez identifier No. 79923) gene were cloned into a plasmid, respectively, driving the firefly luciferase gene from Photinus pyralis. Monoclonal cell lines were generated from human embryonic kidney cells (HEK293, ATCC CRL-1573) cells that contain stably the DNA of the plasmids.

Cell Culture

HEK293 cells were cultured in DMEM (Gibco, Germany) containing 10% FBS (PAA, Germany) and 1% Penicillin/Streptomycin (Pen/Strep, Gibco, Germany). The cells were maintained under 5% CO2 at 37° C. in a humidified atmosphere.

Oct4 or Nanog Stable Reporter HEK293 cells were cultured in in DMEM medium containing high glucose without glutamin, 10% FCS, 1% 1M Hepes-Buffer, 0.5% Penicillin/Streptomycin and 0.5% with fresh 200 mM glutamin(L) before use.

Assay

Luciferase report assay was performed using Beatle juice kit (PJK, Germany) according to the manufacturer instruction. Briefly, Oct4 or Nanog stable reporter Hek293 cells were plated into 24-well tissue culture plates at a density of 200,000 or 300,000 cells per well for 24h. The cells were treated with compounds as indicated in context and harvested with 60 μL Beatle lysis-juice at room temperature for 15 min. The protein concentration was determined by Bradford assay (Sigma, Germany). 20 μL cell lysis was added to 100 μL reaction mixture containing luciferin and ATP, incubated for 3 min and measured by a Luminometer plate-reader. Data were normalized DMSO control, show the mean ±SD of duplicates and are representative of three independent experiments RT-PCR, Primers Quantitative real-time reverse-transcription-PCR was performed according to manufacturer's instructions (Light Cycler, Roche, Germany). Briefly, normal HEK293 cells were treated with compounds as indicated for 48 h. Total RNA was isolated using Qiagen total RNA extraction kit. cDNA was generated by reverse-transcription using AMV reverse transcriptase (Promega, Germany) of equivalent quantities of RNA and qRT-PCR was performed using SYBR Green PCR master mix on Light Cycler 480 (Roche, Germany). The following primer (Eurofins, Germany) pairs were used for the amplification of Oct3/4, Nanog, Sox2, Rex1 and Lin28A, respectively: (Oct3/4) 5s: GAAGTTGGAGAAGGTGGAAC (SEQ ID 01); 3as: GGTGATCCTCTTCTGCTTCAG (SEQ ID 02); (Nanog) 5s: GAACTGTGTTCTCTTCCACC (SEQ ID 03); 3as: CACCTGTTTGTAGCTGAGGTTC (SEQ ID 04); (Sox2): 5s: CAAGACGCTCATGAAGAAGG (SEQ ID 05); 3as: CATGTGCGCGTAACTGTCCATG (SEQ ID 06); (Rex1) 5s: GATCTTCAACGAGTCCACCAG (SEQ ID 07); 3as: GAAAGGTGGGAGATCCTCCTCTTC (SEQ ID 08); (Lin28A) 5s: GTGGATGTCTTTGTGCACCAG (SEQ ID 09); 3as: GACACGGATGGATTCCAGAC (SEQ ID 10). R-Actin 5s: CTGACTACCTCATGAAGATCCTC (SEQ ID 11); 3as: CATTGCCAATGGTGATGACCTG (SEQ ID 12) was used as an endogenous control. Data were normalized to the value of DMSO treated cells showing the mean ±SD of quadruplicates and are representative of two independent experiments

The invention claimed is:

1. A method for inducing a pluripotent mammalian stem cell, comprising contacting a mammalian donor cell with a compound represented by formula 1:

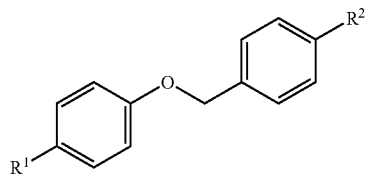

(1)

wherein $R^1$ is $(CH_2)_mE$, with E being CCH or CN and m being 0, 1, or 2, and $R^2$ is selected from F, Cl, Br, $NO_2$, $OR^3$ and $R^3$, with $R^3$ being selected from H, $CH_xF_{3-x}$, wherein x equals 0, 1, 2, or 3.

2. The method according to claim 1, wherein $R^1$ is $CH_2CN$.

3. The method according to claim 1, wherein $R^2$ is $OCF_3$, $OCH_3$ or F.

4. The method according to claim 1, where said compound is:

2-[4-[(4-methoxyphenyl)methoxy]phenyl]acetonitrile (2);

2-[4-[(4-fluorophenyl)methoxy]phenyl]acetonitrile (3) or

2-[4-[[4-(trifluoromethoxy)phenyl]methoxy]phenyl]acetonitrile (4).

5. The method according to claim 1, wherein the mammalian donor cell is a cell derived from skin tissue, bone, blood, muscle, heart, or liver.

6. The method according to claim 1, comprising the steps of:
providing said mammalian donor cell ex-vivo in a cell culture medium;
adding said compound to achieve a defined final concentration of said compound;
maintaining said donor cells under conditions of cell culture for a defined amount of time;
collecting said pluripotent mammalian stem cell.

7. The method according to claim 6, wherein said defined final concentration is between 1 μmol/l and 15 μmol/l.

8. The method according to claim 6, wherein said defined amount of time is between 5 days and 30 days.

9. The method according to claim 6, wherein collecting said pluripotent mammalian stem cells comprises a selection step, whereby said pluripotent mammalian stem cells are selected that
express a gene selected from the group comprised of Nanog, SOX2, LIN28, SSEA-4, TRA-1-60, TRA-1-81, CD133 and Alkaline Phosphatase and/or
do not express CD13.

10. A cell culture medium comprising a compound represented by formula 1:

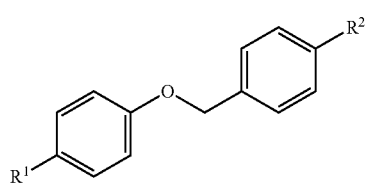

wherein $R^1$ is $(CH_2)_m E$, with E being CCH or CN and m being 0, 1, or 2, and $R^2$ is selected from F, Cl, Br, $NO_2$, $OR^3$ and $R^3$, with $R^3$ being selected from H, $(CH_xF_{3-x}$, wherein x equals 0, 1, 2, or 3.

11. The cell culture medium according to claim 10, wherein $R^1$ is CN.

12. The cell culture medium according to claim 10, wherein $R^2$ is $OCF_3$, $OCH_3$ or F.

13. A cell culture medium according to claim 10, wherein said compound is:
   2-[4-[(4-methoxyphenyl)methoxy]phenyl]acetonitrile (2);
   2-[4-[(4-fluorophenyl)methoxy]phenyl]acetonitrile (3) or
   2-[4-[[4-(trifluoromethoxy)phenyl]methoxy]phenyl]acetonitrile (4).

14. The cell culture medium according to claim 10, wherein said compound has a concentration between 1 μmol/l to 25 μmol/l.

15. A method for inducing OCT4 and NANOG in a cell, comprising contacting a mammalian donor cell with a compound represented by formula 1:

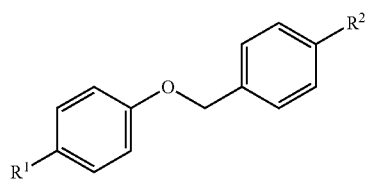

wherein $R^1$ is $(CH_2)_m E$, with E being CCH or CN and m being 0, 1, or 2, and $R^2$ is selected from F, Cl, Br, $NO_2$, $OR^3$ and $R^3$, with $R^3$ being selected from H, $(CH_xF_{3-x}$, wherein x equals 0, 1, 2, or 3.

16. The method according to claim 15, wherein $R^1$ is $CH_2CN$.

17. The method according to claim 15, wherein $R^2$ is $OCF_3$, $OCH_3$ or F.

18. The method according to claim 15, where said compound is:
   2-[4-[(4-methoxyphenyl)methoxy]phenyl]acetonitrile (2);
   2-[4-[(4-fluorophenyl)methoxy]phenyl]acetonitrile (3) or
   2-[4-[[4-(trifluoromethoxy)phenyl]methoxy]phenyl]acetonitrile (4).

19. The method according to claim 15, wherein the mammalian donor cell is a cell derived from skin tissue, bone, blood, muscle, heart, or liver.

\* \* \* \* \*